(12) United States Patent
Kramer et al.

(10) Patent No.: US 11,260,096 B2
(45) Date of Patent: Mar. 1, 2022

(54) COMPOSITIONS FOR CREATINE SUPPLEMENTATION IN CREATINE NON-RESPONDERS

(71) Applicant: ThermoLife International, LLC, Phoenix, AZ (US)

(72) Inventors: Ronald Kramer, Phoenix, AZ (US); Alexandros Nikolaidis, Nea Kallikratia (GR)

(73) Assignee: ThermoLife International, LLC, Signal Hill, CA (US)

( * ) Notice: Subject to any disclaimer, the term of this patent is extended or adjusted under 35 U.S.C. 154(b) by 0 days.

(21) Appl. No.: 16/913,973

(22) Filed: Jun. 26, 2020

(65) Prior Publication Data

US 2020/0405799 A1 Dec. 31, 2020

Related U.S. Application Data

(60) Provisional application No. 62/868,755, filed on Jun. 28, 2019.

(51) Int. Cl.
| | |
|---|---|
| *A61K 36/48* | (2006.01) |
| *A61K 31/198* | (2006.01) |
| *A23L 33/175* | (2016.01) |
| *A23L 33/105* | (2016.01) |

(52) U.S. Cl.
CPC ............ *A61K 36/48* (2013.01); *A23L 33/105* (2016.08); *A23L 33/175* (2016.08); *A61K 31/198* (2013.01)

(58) Field of Classification Search
CPC .......................... A23L 33/175; A61K 31/198
See application file for complete search history.

(56) References Cited

U.S. PATENT DOCUMENTS

| | | | |
|---|---|---|---|
| 8,703,719 B1 * | 4/2014 | Abraham | ............. A61K 36/185 514/23 |
| 2002/0001611 A1 | 1/2002 | Howard et al. | |
| 2011/0313042 A1 * | 12/2011 | Kramer | ................... A61P 21/00 514/565 |
| 2016/0303061 A1 | 10/2016 | Faulkner et al. | |

FOREIGN PATENT DOCUMENTS

WO WO-2007047041 A2 * 4/2007 ......... G01N 33/5088

OTHER PUBLICATIONS

"Weekly Fitness Tips". Web Publication Date: Apr. 15, 2016 [Retrieved from the Internet on: Apr. 24, 2021]. Retrieved from: <URL: https://weeklyfitnesstips.com/how-to-build-big-muscles-fast/>. 7 pages. (Year: 2016).*

Galvan, E. et al., Acute and chronic safety and efficacy of dose dependent creatine nitrate supplementation and exercise performance, Journal of the International Society of Sports Nutrition, 2016, doi: 10.1186/s12970-016-124-0, abstract, p. 7-13, 16-18, 13.

Alraddadi, E. et al., Absolute Oral Bioavailability of Creatine Monohydrate in Rats: Debunking a Myth, Pharmaceutics, 2018, doi: 10.3390, pharmaceutics10010031.

* cited by examiner

*Primary Examiner* — Amy L Clark
(74) *Attorney, Agent, or Firm* — Booth Udall Fuller, PLC; Pacer K. Udall

(57) ABSTRACT

Disclosed herein are methods for creatine supplementation for human subjects, particularly creatine non-responders.

8 Claims, 4 Drawing Sheets

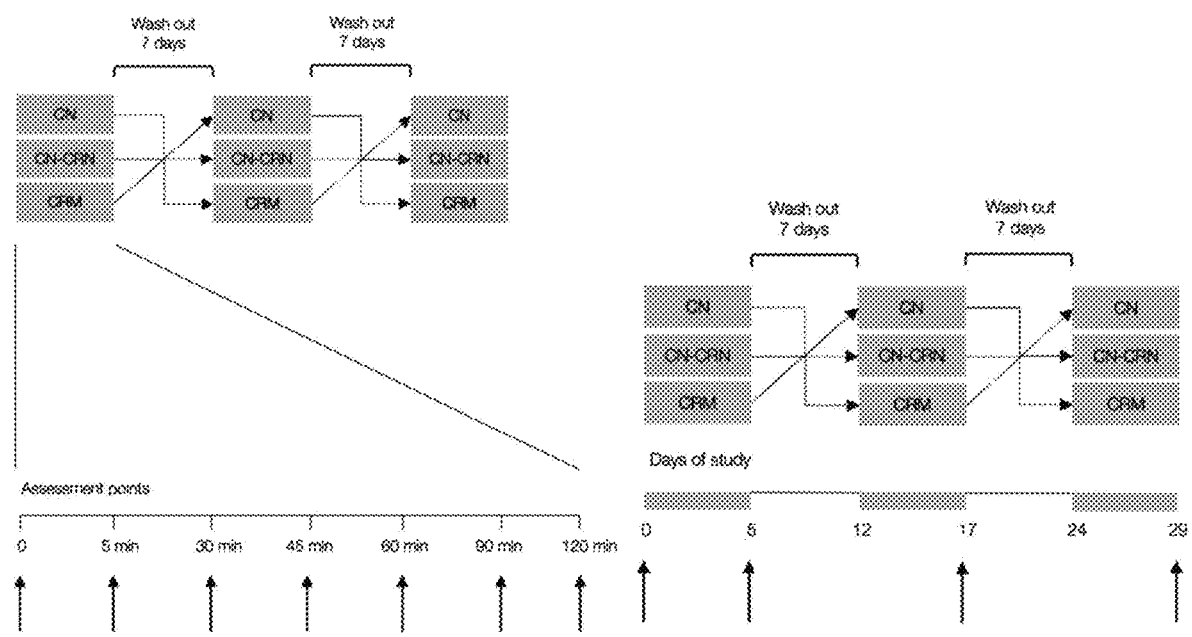
Fig. 1A
Single-dose (3 grams) trial
Fig. 1B
5-day intervention (3 grams per day)
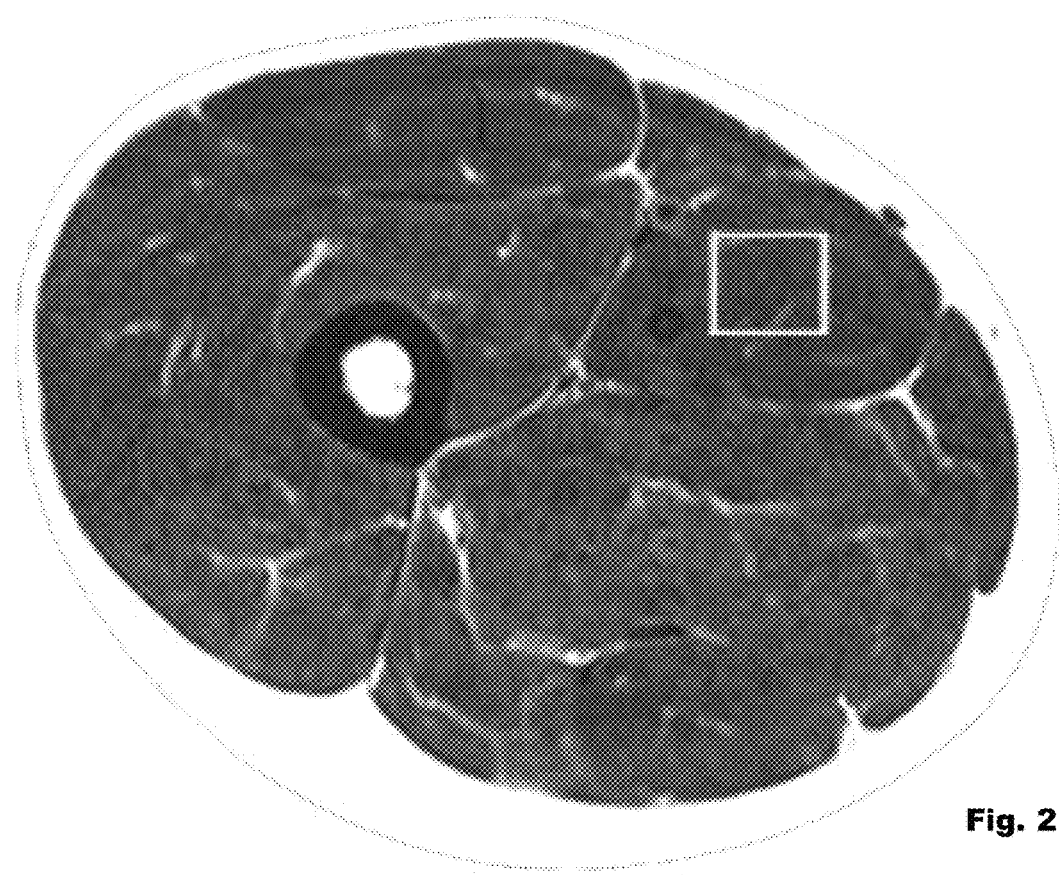
Fig. 2

Fig. 5
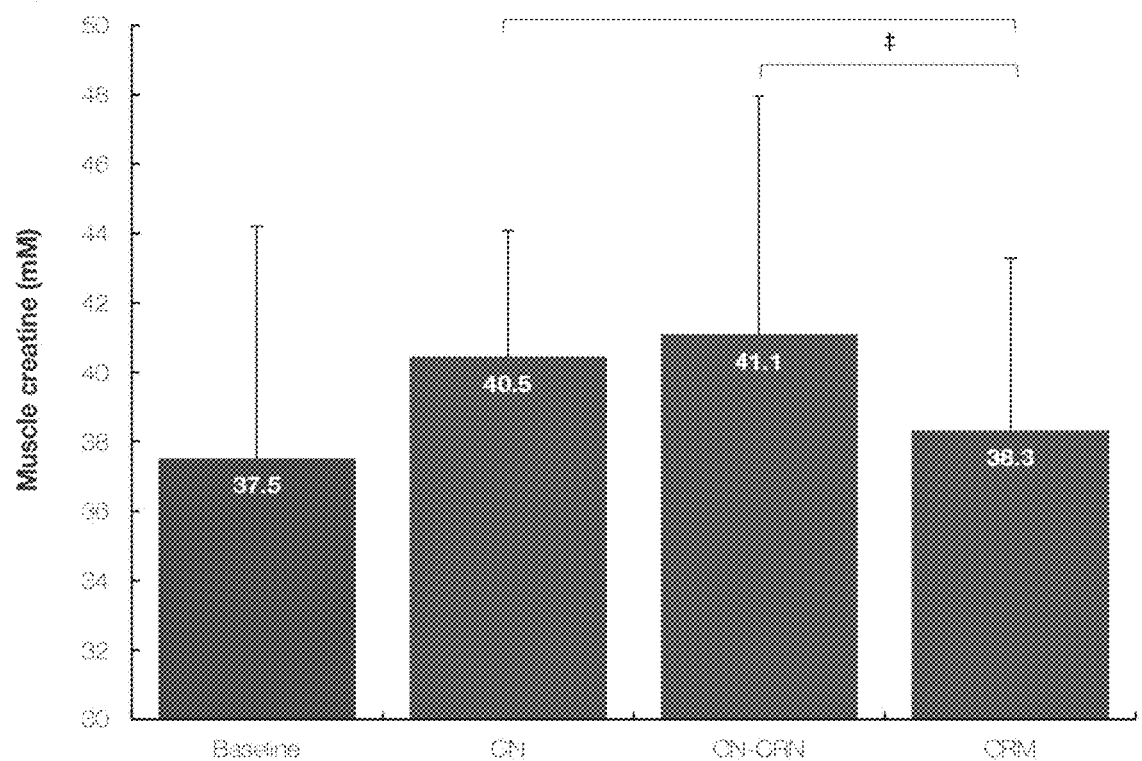
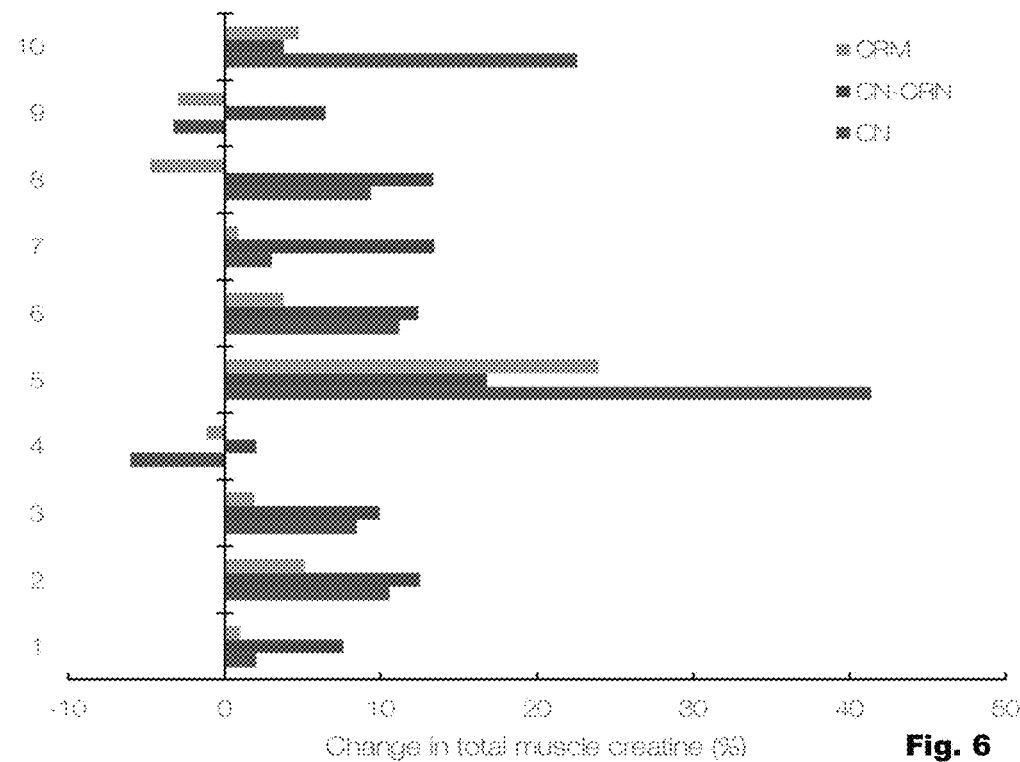
Fig. 6

COMPOSITIONS FOR CREATINE SUPPLEMENTATION IN CREATINE NON-RESPONDERS

CROSS REFERENCE TO RELATED APPLICATIONS

This application claims the benefit of and priority to U.S. provisional patent application 62/868,755, filed Jun. 28, 2019, the entireties of the disclosure of which are hereby incorporated by this reference.

BACKGROUND

Creatine (Cr) is an endogenous nutrient that occurs in various tissues of mammals, for example, in liver, kidneys, muscular tissue, brain tissue, and blood. It appears in a free state as well as in the form of creatine phosphate. Creatine phosphate (CrP) and creatine are allosteric regulators of cell processes. Creatine enhances the energy tissue metabolism by increasing the energy reserve of ATP in the muscle and nerve cells.

In a cell's mitochondria, creatine interacts reversibly with adenosine triphosphate (ATP) through the action of a creatine kinase enzyme that catalyzes the formation of creatine phosphate and adenosine diphosphate (ADP). Upon consumption of ATP in a cell, a great amount of ADP is released, which leads to a transfer of ortho-phosphate from CrP to ADP, and the initial ratio between ATP and ADP remains. Due to the high affinity of creatine kinase to ADP, this process continues until a creatine phosphate concentration falls below several tens micromolar. This interaction between creatine and ATP maintains the ATP concentration at a constant level at the moments of intense ATP consumption. While other processes exist for replenishing ATP, such as glycolysis or oxidative phosphorylation, these processes refill ATP noticeably slower than the interaction between ATP and creatine.

CrP represents a reserve of macroergic phosphate for maintaining the membrane potential, activation of metabolites or contractive activity of a cell. CrP maintains the ATP level during a period of increasing of energy consumption in a cell, for example, via restoring an ortho-phosphate residue on ADP. Like glycogen, CrP is one of the basic sources of the high-energy phosphates transformation cycle and thereby participates in oxidative phosphorylation of glucose that provides liberation of energy necessary for the functionality of muscular tissue cells, including skeletal muscles and the cardiac muscle. Since CrP provides for regeneration of ATP with a significant speed, an increase of creatine amount in the muscles raises the muscles capacity of CrP, enhances the muscles workability, and increases the muscle bulk.

It has been shown that oral administration of creatine increases the total creatine content in an organism. In particular, administration of creatine monohydrate at dosages up to 30 g for a few days increases the total creatine content in skeletal muscles of a human subject by more than 20%. These properties of creatine make the usage of creatine monohydrate as a dietary supplement or food additive attractive, especially as an addition to the diet of an athlete. As described in the Published International Patent Application WO 94/02127, creatine monohydrate in a daily dose 15 g was administered for at least two days for increasing the muscle force. Nowadays creatine is also recommended as a dietary supplement or food additive for elderly people and vegetarians, as these sections of the population tend to have decreased or low creatine level in their muscles.

Besides the use in the dietary supplement and food industry, creatine and creatine phosphate have wide applications in medicine. For example, creatine and creatine phosphate are recommended for the treatment of nervous system diseases such as diabetic and toxic neuropathies, Alzheimer's disease, Parkinson's disease, and stroke, and also disturbances of metabolism such as hyperglycemia and diabetes mellitus (see U.S. Pat. Nos. 6,706,764 and 6,193,973). Oral administration of creatine has also been disclosed to be useful in the treatment of cardiac insufficiency and respiratory failure (International Published Patent Application WO 98/22099) and of asthma (U.S. Pat. No. 6,093,746). Additionally, creatine phosphate has been disclosed as being useful for the treatment of cardiovascular diseases and for the treatment of new-growth tissue (U.S. Pat. No. 5,219,846).

However, a large problem with creatine supplementation in the general populace is a sub-population referred to as "creatine non-responders." This sub-population do not gain any ergogenic benefit from creatine when it is supplemented alone. Based on Greenhaff et al. (Greenhaff et al., *Am. J. Physiol.* 1994, 2 66 (5 Pt 1): E745-30), approximately 20-30% of individuals "do not respond" to creatine supplementation, which is defined as those subjects with less than a 10 mmol/kg dw increase in resting total muscle creatine following five days of creatine ingestion at 20 g/day. Creatine non-responders generally have higher preload levels of phosphocreatine, less type II muscle fibers, small preload muscle cross-sectional area (CSA), and lower fat-free mass (Syrotuik and Bell, *J Strength Cond Res.* 2004, 18(3): 610-7). These individuals show minimal, if any, increase in muscle creatine by creatine loading and no increase in athletic performance, endurance or any other of the benefits associated with creatine supplementation. This sub-population of creatine non-responders buttresses the position that creatine supplementation does not provide any physiological benefits. Even if creatine non-responders tried creatine supplementation, they would not seek to continue as they would not have felt any effect or received any benefit from creatine supplementation.

SUMMARY OF THE INVENTION

Described herein are methods of creatine supplementation. In some embodiment, methods for increasing oral bioavailability of creatine in a human are disclosed. In other embodiments, methods of increasing creatine absorption in muscles from ingested creatine are disclosed. The methods comprise co-administering to a human subject a supplemental amount of creatine, an effective amount of creatinine, and a source of nitrate anion ($NO_3^-$) providing an effective amount of nitrate anion ($NO_3^-$). In some aspects, the human subject is a creatine non-responder. In some implementations, the human subject is administered a composition comprising the supplemental amount of creatine, the effective amount of creatinine, and the source of nitrate anion ($NO_3^-$). In some embodiments, the supplemental amount of creatine is at least 500 mg, the effective amount of creatinine is at least 500 mg, and the effective amount of the nitrate anion ($NO_3^-$) is at least 50 mg. In other embodiments, the supplemental amount of creatine is at least 1000 mg, the effective amount of creatinine is at least 1000 mg, and the effective amount of nitrate anion ($NO_3^-$) is at least 100 mg. In yet other embodiments, the supplemental amount of creatine is at least 2 grams, the effective amount of creatinine is at least 2 grams, and the effective amount of nitrate anion ($NO_3^-$) is at least 500 mg. In certain embodiments, the supplemental amount of creatine is at least 5 grams, the effective amount of creatinine is at least 3 grams, and the effective amount of nitrate anion ($NO_3^-$) is at least 1000 mg. In particular embodiments, the supplemental amount of creatine is at least between 500 mg and 20000 mg, the effective amount of creatinine is at between 500 mg and 30000 mg, and the effective amount of the nitrate anion ($NO_3^-$) is at between 50 mg and 3000 mg.

In some methods of providing creatine supplementation in a human subject, the method comprises administering to the human subject an effective amount of nitrate anion ($NO_3^-$) and an effective amount of creatinine. In some embodiments, wherein the effective amount of creatinine is at least 500 mg and the effective amount of nitrate anion ($NO_3^-$) is at least 50 mg. In other embodiments, the effective amount of creatinine is at least 1000 mg and the effective amount of nitrate anion ($NO_3^-$) is at least 100 mg. In still other embodiments, the amount of creatinine is at least 2 grams and the effective amount of nitrate anion ($NO_3^-$) is at least 500 mg. In certain embodiments, the effective amount of creatinine is at least 3 grams and the effective amount of nitrate anion is at least 1000 mg. In some implementations, the method further comprises administering an effective amount of creatine, for example, wherein the effective amount of creatine is at least 500 mg, at least 1000 mg, at least 2 grams, or at least 5 grams.

Methods of safely administering creatinine to a human subject are also disclosed. The method comprising co-administering to the human subject creatinine with an effective amount of creatine and an effective amount of nitrate anion ($NO_3^-$). The human subjects the human subject displays no clinically significant elevation in liver enzymes or clinically significant reduction in eGFR. In some implementations, creatinine is co-administered with an effective amount of creatine and an effective amount of nitrate anion ($NO_3^-$) for a period of 5 days or longer.

DESCRIPTION OF THE DRAWINGS

FIGS. 1A and 1B depicts the study protocols for a single-dose trial (FIG. 1A) and a 5-day intervention (FIG. 1B). In FIG. 1A, the vertical arrows indicate sampling intervals for serum creatine and creatinine. In FIG. 1B, the vertical arrows indicate sampling intervals for muscle creatine and clinical biochemistry. Abbreviations: creatine nitrate (CN); creatine nitrate plus creatinine (CN-CRN); and creatine monohydrate (CRM).

FIG. 2 depicts a cross-section of the right vastus medialis muscle. The white-line square shows the segment of right vastus medialis muscle processed with MRS.

FIG. 5 depicts the total muscle creatine levels at baseline and five days after the five-day intervention for creatine nitrate (CN), creatine nitrate plus creatinine (CN-CRN), and creatine monohydrate (CRM) trials. Values are mean±SD. † indicates significant difference for percentage change in muscle creatine levels between CN and CRM trials (P=0.01). ‡ indicates significant difference for percent change in muscle creatine levels between CN-CRN and CRM trials (P=0.008).

FIG. 6 depicts the individual changes (%) in total muscle creatine levels from baseline to 5-day follow-up for creatine nitrate (CN), creatine nitrate plus creatinine (CN-CRN), and creatine monohydrate (CRM) trials. Subjects 4, 8, and 9 are creatine non-responders.

DESCRIPTION OF THE INVENTION

Figure 3:
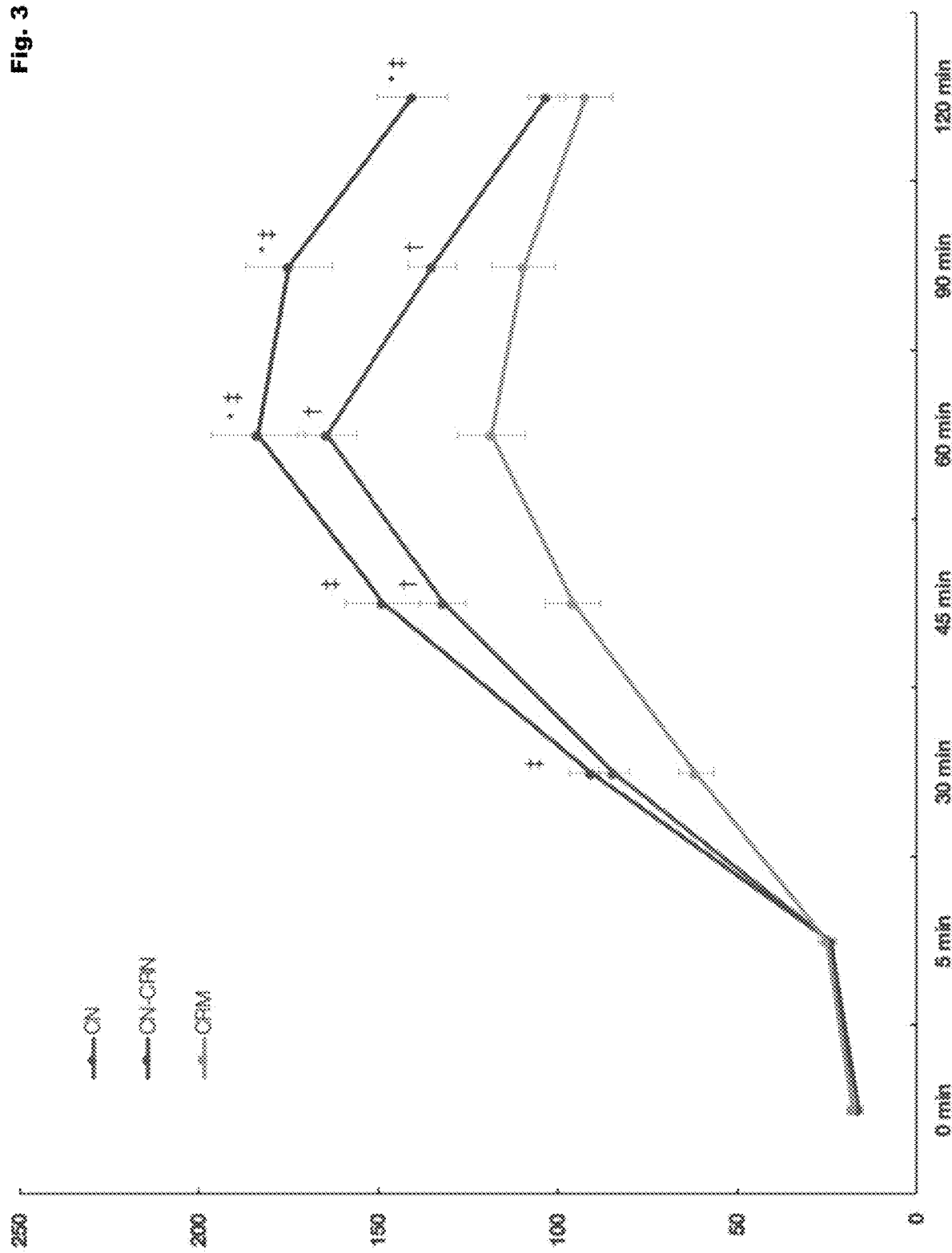
FIG. 3 depicts the changes in serum creatine levels during the course of the single-dose study. Abbreviations: creatine nitrate (CN); creatine nitrate plus creatinine (CN-CRN); and creatine monohydrate (CRM). * indicates significant difference CN vs. CN-CRN at P<0.05; † indicates significant difference CN vs. CRM at P<0.05; and ‡ indicates significant difference CN-CRN vs. CRM at P<0.05.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that implementations of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "about" refers to a deviation up to but not more than 10% of the given value, for example a deviation of 10%, 7.5%, 5%, 4%, 3%, 2%, 1%, 0.5%, or 0.1% of the given value.

As used herein, the term "effective amount" refers to an amount that induces a measurable or observable change. For example, in certain embodiments, an effective amount of nitrate refers to an amount of nitrate that increases the stabilizing effect of creatinine on creatine in an aqueous composition. In some aspects, the effective amount of nitrate refers to an amount of nitrate that increase conversion rate of creatinine to creatine.

As used herein, the term "supplemental amount" of creatine refers to an amount of creatine that is greater than the amount of creatine that would be ingested from a conventional diet.

As used herein, the term "a source of nitrate anion ($NO_3^-$)" include all forms of inorganic nitrate that, when dissolved in water or a similar polar solvent will wield the nitrate anion ($NO_3^-$). For example, a source of nitrate anion ($NO_3^-$) includes nitrate salts such as creatine nitrate, potassium nitrate, sodium nitrate, and the like. In other aspects, a source of nitrate anion ($NO_3^-$) includes vegetable extracts, juices, powders, and the like standardized for nitrate content from vegetables that contain high levels nitrate. In another aspects, a source of nitrate anion ($NO_3^-$) includes nitric acid solutions and the like.

As used herein, the term "creatine non-responder" references a sub-population of the general populace who do not gain any health or ergogenic benefit from creatine when creatine (or its salt) alone is the source of creatine supplementation. In some aspects, a creatine non-responder is a human subject who has less than a 10 mmol/kg dw increase in resting total muscle creatine following five days of ingestion 20 g creatine per day. In other aspects, creatine non-responders have higher preload levels of phosphocreatine, less type II muscle fibers, small preload muscle cross-sectional area (CSA), and lower fat-free mass.

The disclosure relates to the surprising discovery that co-administering creatine with a source of nitrate anion ($NO_3^-$) and creatinine resulted in increased muscle stores of creatine in people that would be considered creatine non-responders. A possible explanation for the surprising effect of co-administering creatine with a source of nitrate anion ($NO_3^-$) and creatinine on creatine levels in muscle may be that the nitrate ion enhances the conversion of creatinine to creatine and forces the equilibrium of creatine and creatinine towards creatine. Accordingly, the disclosure relates to improved methods of providing creatine supplementation in a human subject, preferably in a human subject that is a creatine non-responder. In one aspect, the disclosure describes a method of providing creatine supplementation to a creatine non-responder. In another aspect, the disclosure described a method of increasing creatine content in muscle in a human subject, preferably a human subject who is a creatine non-responder. Also disclosed are methods for increasing oral bioavailability of creatine in a human and methods of increasing creatine absorption by muscles from ingested creatine.

The methods comprising co-administering to a human subject with a supplemental amount of creatine, an effective amount of creatinine, and a source of nitrate anion ($NO_3^-$) providing an effective amount of nitrate anion ($NO_3^-$). In some implementations, the creatine non-responder or the human subject is administered a composition comprising the supplemental amount of creatine; the effective amount of creatinine; and the source of nitrate anion ($NO_3^-$). In some embodiments, the human subject is orally administered the supplemental amount of creatine, the effective amount of creatinine, and the source of nitrate anion ($NO_3^-$).

In certain implementations, the molar ratio of the supplementation amount of creatine and the effective amount of creatinine or nitrate anion ($NO_3^-$) is between about 20:1 and about 1:9, for example, between about 10:1 and 1:1, between about 3:1 and 1:3, between about 2:1 and about 1:4. In a preferred implementation, the molar ratio of the supplementation amount of creatine and the effective amount of nitrate anion ($NO_3^-$) is about 1:1. In some embodiments of the methods, the human subject is administered a supplemental amount of creatine of at least about 500 mg, an effective amount of creatinine of at least about 500 mg, and an effective amount of the nitrate anion ($NO_3^-$) of at least about 50 mg. For example, in one implementation, the supplemental amount of creatine is at least about 1000 mg, the effective amount of creatinine is at least about 1000 mg, and the effective amount of nitrate anion ($NO_3^-$) is at least about 100 mg. In another implementation, the supplemental amount of creatine is at least about 2 grams, the effective amount of creatinine is at least about 2 grams, and the effective amount of nitrate anion ($NO_3^-$) is at least about 500 mg. In still another implementation, the supplemental amount of creatine is at least about 5 grams, the effective amount of creatinine is at least about 3 grams, and the effective amount of nitrate anion ($NO_3^-$) is at least about 1000 mg.

The disclosure also describes a method of providing creatine supplementation in a human subject by encouraging the conversion of creatinine to creatine in vivo. The method comprises administering to the human subject an effective amount of nitrate anion ($NO_3^-$) and an effective amount of creatinine. In some implementations, the effective amount of creatinine is at least about 500 mg and the effective amount of nitrate anion ($NO_3^-$) is at least about 50 mg. In other implementations, the effective amount of creatinine is at least about 1000 mg and the effective amount of nitrate anion ($NO_3^-$) is at least about 100 mg. In still other implementations, the amount of creatinine is at least about 2 grams and the effective amount of nitrate anion ($NO_3^-$) is at least about 500 mg. In some aspects, the effective amount of creatinine is at least about 3 grams and the effective amount of nitrate anion ($NO_3^-$) is at least about 1000 mg.

The method of encouraging conversion of creatinine to creatine in vivo is not hindered by administration of creatine. Accordingly, in some implementations, the method further comprises administering to the human subject an amount of creatine. In some aspects, the amount of creatine is at least about 500 mg, at least about 1000 mg, at least about 2 grams, or at least about 5 grams. In certain implementations, the molar ratio of the amount of creatine and the effective amount of creatinine or nitrate anion ($NO_3^-$) is between about 20:1 and about 1:9, for example, between about 10:1 and 1:1, between about 3:1 and 1:3, between about 2:1 and about 1:4. In a preferred implementation, the molar ratio of the amount of creatine and the effective amount of nitrate anion ($NO_3^-$) is about 1:1.

Another surprising benefit of the creatine compositions described herein is that the combination of creatinine, creatine, and a source of nitrate anion ($NO_3^-$) increases the safety and stability, especially in an aqueous composition, of a creatine and creatinine. In one aspects, in the presence of a source of low amounts of creatinine would be required to achieve stabilization of creatine. While creatine's safety has been well established by multiple studies, creatinine's safety is still questionable as far as regulatory agencies are concerned. Thus lesser amounts of creatinine to achieve the effects of stabilizing creatine and enhancing its bioavailability are desired. Accordingly, also described herein are methods of safely administering creatinine to a human subject comprising co-administering to the human subject creatinine with an effective amount of creatine and an effective amount of nitrate anion ($NO_3^-$). Notably, the human subject displays no clinically significant elevation in liver enzymes or clinically significant reduction in eGFR. In some implementations, creatinine is co-administered with an effective amount of creatine and an effective amount of nitrate anion ($NO_3^-$) for a period of 5 days or longer.

EXAMPLES

The disclosure is further illustrated by the following examples that should not be construed as limiting. The contents of all references, patents, and published patent applications cited throughout this application are incorporated herein by reference in their entirety for all purposes.

Example 1

Creatine anhydrous and creatinine at various concentrations at pH 4.4 were produced by the applicants to find if creatinine could stabilize creatine without the presence of nitrate. It was found that after one month of storage, the solution that contained 3 grams creatine and 8 grams creatinine was more than 10% stable after storage for one month at room temperature. This equals to a molar ratio of about 1:2.7 creatine:creatinine ratio to achieve a stable mixture for long storage. This is problematic in many accounts. First of all, the amount of creatinine is very high. Secondly to achieve a 5-gram creatine content, a whooping 13.5 grams of creatinine would be required giving a total of 21.5 grams of creatine and creatinine. At the typical energy drink sizes of 8-16 oz, such an amount of powder could not be dissolved, especially under refrigerated storage where the solubility of creatine and creatinine is reduced. It was also found that the amount of creatine would vary depending on whether the solution was stored in a cool environment (about 2° C.) versus room temperature. That would make formulating a creatine drink with precise labeling and dosing of the creatine content even harder. By contrast, as the applicants have shown with their creatine nitrate and creatinine solutions, the amount of creatinine needed to stabilize creatine is much less with the co-existence of a sufficient amount of nitrate ion in the solution. The molar ratio of creatine-creatinine needed to achieve creatine stability is only 1.7 when 5 grams of creatine nitrate were mixed with 5 grams of creatinine, giving a molar ratio of creatine:creatinine:nitrate of about 1:1.7:1. Thus it was surprisingly found that the nitrate ion can enhance the stabilizing effect of creatinine on creatine. As suggested from the results of Example 2, the ability of nitrate anion ($NO_3^-$) to enhance the conversion of creatinine to creatine could also happen in vivo.

Example 2

A study was performed to evaluate the effects of creatine nitrate administration with creatinine in creatine bioavailability and creatine muscle stores.

Ten healthy young men (age 23.6±2.9 years, body mass index 23.8±1.5 kg/m') were recruited and signed informed consent to voluntarily participate in this double-blind, crossover, randomized controlled trial. All experimental procedures were approved by the local institutional review board, and the study was conducted in accordance with the Declaration of Helsinki. All participants had no history of creatine supplementation (or other dietary supplements) within the 4 weeks before the study commenced. All participants also had no acute or chronic diseases as evaluated by pre-participation health check and blood profiles. All participants were required to maintain their normal activity patterns and diet during the study. The participants were required to not engaged in any exhaustive exercise 24 hours before the study commenced.

The participants were assigned to receive either CN-CRN (3 grams of creatine nitrate and 3 grams of creatinine), 3 grams of CN (creatine nitrate), or 3 grams of CRM (creatine monohydrate) by oral administration in a single-dose pharmacokinetics experiment and for a 5-day intervention (FIGS. 1A and 1B).

Washout period of 7 days was employed between all trials to prevent the residual or carry-over effects of treatments across study periods. For the single-dose experiment, participants were administered a liquid composition that was prepared by a researcher by dissolving a powder of their respective treatment compounds in 150 mL of lukewarm water. For the 5-day intervention, the participants received five powder sachets (one per day) containing an treatment compounds. The participants were advised to stir the content of the sachet into 150 mL of lukewarm water until the powder has dissolved and to drink the liquid composition about 30 minutes before breakfast. Creatine nitrate was supplied by ThermoLife International LLC (Phoenix, Ariz.), while creatine monohydrate (CreaPure®) was purchased from a retailer store (ATP Sport, Belgrade). Creatinine anhydrous has been produced from creatine monohydrate in an autoclave (Memmert UF 55, Schwabach, Germany) at 160° C. for 72 hours, with creatinine purity>99% in a final powder, as determined by NMR spectroscopy (Bruker Avance III 400, Billerica, Mass.). Clinical assessments for both experiments were carried out between 08:00 and 12:00 after an overnight fast of 12 hours. Venous blood samples were drawn at each time point (7 points in total) for a single-dose experiment, and serum analyzed for creatine and creatinine by modified LC-MS/MS (1200 Series LC System; Agilent Technologies Inc., Santa Clara, Calif., USA). To control for variance based on different hydration levels, all participants were restricted from water ingestion between the time of collecting the baseline sample and 120 minutes after administration of the treatment. For 5-day experiment, venous blood samples were drawn at baseline and at the various follow-up times, with serum analyzed for liver enzymes by an automated analyzer (Randox Laboratories Ltd., Crumlin, UK).

Estimated glomerular filtration rate (eGFR) was calculated by the abbreviated MDRD equation (Stevens et al., *Am J Kidney Dis.* 2007; 50: 21-35). Proton magnetic resonance spectroscopy (MRS) was performed on 1.5 Tesla Avanto scanner (Siemens, Erlangen, Germany) using a flexible phased array body-matrix coil, with metabolite spectra in the right vastus medialis muscle processed with AMARES. A standardized volume of interest (20×20×20 mm3) was positioned within the right vastus medialis muscle with attention to avoid blood vessels, subcutaneous and other fat, and osseous structures (FIG. 2). After local shimming and gradient adjustments, data were obtained with 256 data points and 32 non-water-suppressed scans using a point-resolved spectroscopic sequence (PRESS) to acquire a single volume (TR/TE, 2000/135 ms). Twelve datasets were obtained for each individual yielding a total of 120 spectra in this study. In vivo metabolite concentrations were calculated using the muscle water signal as an internal intensity reference (Wang et al., *J Magn Reson.* 2014, 243: 81-84). The spectra were fitted in the time domain using a nonlinear least squares algorithm (AMARES) in the Java-based magnetic resonance user interface (jMRUI) software package. The peak integral values of the total creatine (creatine plus phosphocreatine) signal at 3.0 ppm and the non-suppressed water signal at 4.7 ppm were quantified using curve-fitting to Gaussian lines. The signals were corrected for T1 and T2 relaxation using the T1 and T2 relaxation times as previously described (Varghese et al., *NMR Biomed.* 2015, 28(8): 998-1008). Finally, possible adverse events of the intervention (e.g. muscle cramps, bloating, diarrhea) were evaluated via open-ended questionnaires administered during the trial.

Statistical Analyses

A total number of subjects (n=10) was calculated with effects size set at 0.9, two-tail alpha level 0.05 and study power 0.80, with primary outcome was the change in total creatine levels in the serum assessed at baseline and at 120 minutes post-administration. Two-way ANOVA design for repeated measures (treatment vs. time) was used to establish if any significant differences existed between three interventions ingested during the experiment.

Where significant differences were found, the Tukey post-hoc test was employed to identify the differences. The area under the concentration-time curve (AUC) for serum creatine and creatinine were calculated using the linear-log trapezoidal method, with AUCs compared with one-way ANOVA. The significance level was set at P<0.05. Data were analyzed using the SPSS program (SPSS Inc., Chicago, Ill., USA).

Results

A. Single-Dose Experiment

All participants completed the trial. No participant reported any side effects, although the odors of CN-CRN and CN formulations were reported to be unpleasant by 8 of 10 subject (80%). The compliance for all three groups was 100%. Changes in serum creatine levels during the course of the single-dose experiment are depicted in FIG. 3. All three interventions induced a sharp rise in serum creatine concentrations starting at 5 minutes post-administration with peak levels achieved after 60 min post-administration in all three groups, which was followed with a moderate reduction in creatine levels by the end of sample collection. The average creatine concentrations at 60 minutes post-administration were significantly higher in CN-CRN group (183.7±15.5 µmol/L), as compared to CN group (163.8±12.9 µmol/L) and CRM group (118.6±12.9 µmol/L) (P<0.001). In addition, CN-CRN resulted in overall higher levels of creatinine in the blood to creatine comparing to either CN or CrM after single-dose intervention, as evaluated with AUC calculation (701.1±62.1 µmol/L)×min vs. 622.7±62.9 µmol/L)×min vs. 466.3±47.9 µmol/L)×min; P<0.001).

Figure 4:
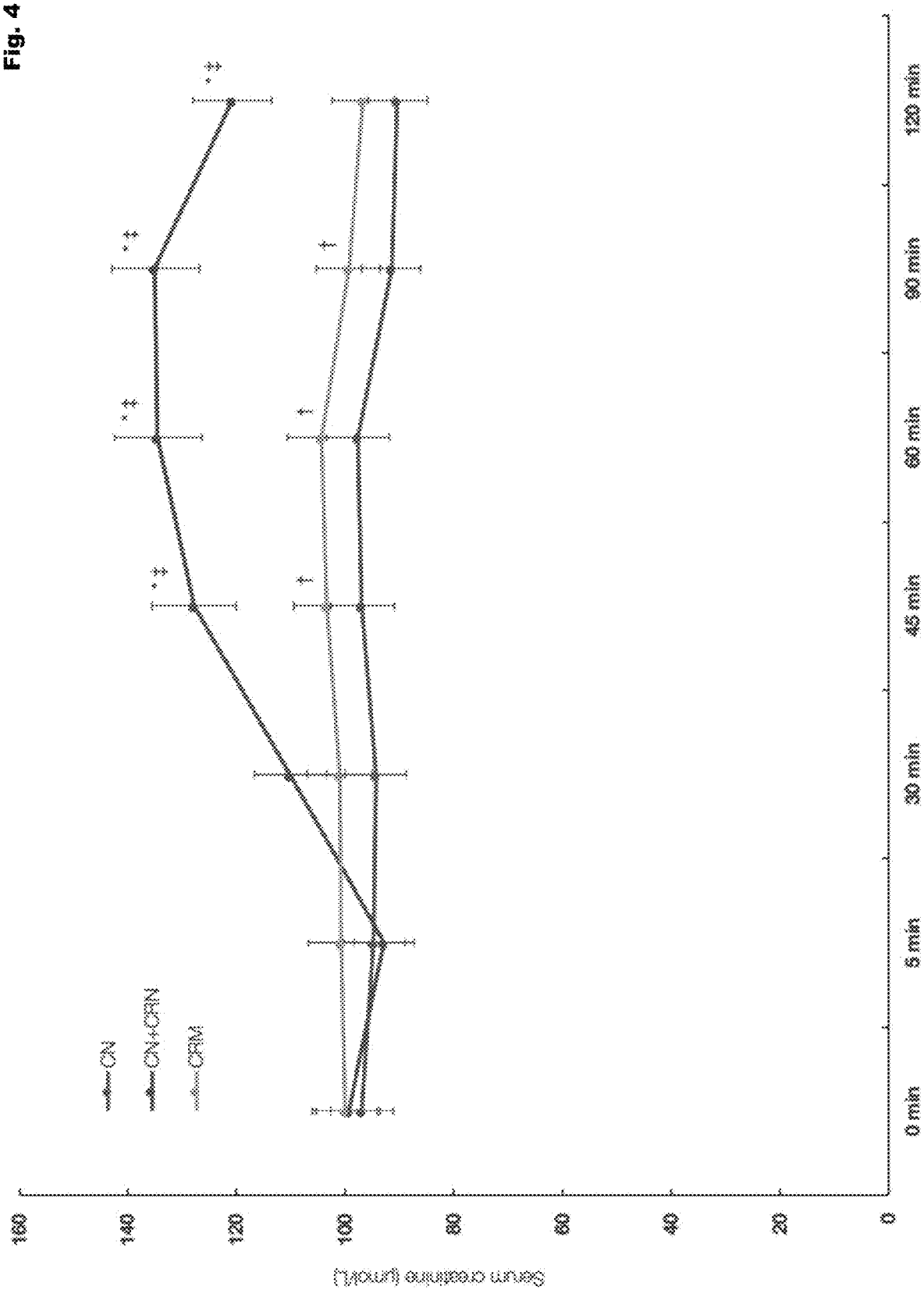
FIG. 4 depicts the changes in serum creatinine levels during the course of the single-dose study. Abbreviations: creatine nitrate (CN); creatine nitrate plus creatinine (CN-CRN); and creatine monohydrate (CRM). * indicates significant difference CN vs. CN-CRN at P<0.05; † indicates significant difference CN vs. CRM at P<0.05; and ‡ indicates significant difference CN-CRN vs. CRM at P<0.05.

Serum creatinine remained essentially unchanged during the study in CN and CRM groups (FIG. 4). However, serum creatinine increased significantly in CN-CRN group, with peak values noted after 90 minutes post-administration (135.0±17.1 µmol/L) at an increase of 21.5±13.0% from the baseline values. AUC analysis for creatinine revealed a significant difference between CN-CRN, CN and CRM groups, respectively (710.4±49.2 µmol/L)×min vs. 568.9±24.7 µmol/L)×min vs. 607.5±37.7 µmol/L)×min; P<0.001), respectively.

B. Five-Day Intervention

All participants completed the 5-day intervention, and the compliance with the regimen was 100% for CN group, 98.0% for CN-CRN group, and 100% for CRM group, with unused powder sachets used to determine participants' compliance. A single participant (age 30, weight 69.5 kg) reported a single episode of irregular non-diarrheal bowel movements each day throughout the intervention with CN, and also for the first two days after CN-CRN intervention, with the episode typically appeared about 2 hours after an administration. Another participant (age 19, weight 78.7 kg) reported excessive sleepiness in the course of CN intervention. Finally, a third participant (age 22, weight 80.0 kg) reported episodes of bloating throughout CRM intervention. The other seven participants reported no side effects of either intervention. The effects of different interventions on selected safety biomarkers are depicted in Table 1. No significant differences were observed between treatment groups in alanine aminotransferase (ALT) and aspartate aminotransferase (AST) among participants receiving CN, CN-CRN or CRM (P>0.05). Liver enzymes remained in the normal reference ranges throughout the study, with no participant having abnormal liver blood tests (e.g. AST>40 units/L, and/or ALT>56 units/L). Supplemental CN-CRN significantly decreased eGFR at 5-day follow up, as compared to other interventions (P=0.004), with the average reduction was 14.8±7.7% (95% confidence interval [CI]; from 9.3 to 20.3). Eight out of ten participants (80.0%) receiving CN-CRN intervention experienced mildly reduced kidney function (eGFR 60-89 mL/min/1.73 m$^2$) as compared to 40.0% in CN group and 30.0% in CRM group. Nevertheless, no participant faced clinically relevant reduction in eGFR (<60 mL/min/1.73 m$^2$) throughout the course of the trial. The highest reduction in eGFR (23.9%) was noted in a participant (age 30, 69.5 kg) receiving CN-CRN intervention.

TABLE 1

Changes in liver enzymes and estimated glomerular filtration rate (eGFR) during the study. Values are mean ± SD.

| | Baseline | At 5-day follow-up | | | P * |
| --- | --- | --- | --- | --- | --- |
| | | CN | CN-CRN | CRM | |
| Aspartate aminotransferase (IU/ml) | 21.0 ± 2.6 | 20.1 ± 1.9 | 20.5 ± 3.2 | 20.2 ± 2.2 | 0.940 |
| Alanine aminotransferase (IU/ml) | 18.2 ± 2.4 | 21.8 ± 6.6 | 21.4 ± 5.7 | 20.9 ± 3.4 | 0.949 |
| eGFR (mL/min/1.73 m$^2$) | 97.8 ± 8.3 | 89.8 ± 8.1 | 83.3 ± 10.6 | 91.7 ± 8.3 | 0.004 |

* P value from two-way mixed ANOVA (treatment vs. time interaction)

All three interventions induced a notable rise in total creatine content in muscle from baseline levels (37.5±6.7 mM) after the five-day intervention, with two-way ANOVA with repeated measures revealed a significant effect of intervention (P=0.01), indicating different concentration-changes in skeletal muscle creatine dependent on the intervention administered (FIG. 5). The results show CN-CRN intervention causing the highest average increase in total muscle creatine levels (9.6%; 95% CI from 6.4 to 13.2), followed by CN (8.0%, 95% CI from 0.1 to 19.7), and CRM trial (2.1%, 95% CI from −2.5 to 8.9), with both CN-CRN and CN causing statistically significantly increase to muscle creatine concentrations compared to CRM (P<0.01). While 2 out of 10 participants were found to be non-responsive to CN intervention (20.0%) (e.g. no amplification in muscle creatine levels found at follow up), and 3 participants out of 10 were non-responsive in CRM trial (30%), no non-responders were found after CN-CRN intervention, with individual upswing in total muscle creatine varied from 2.0% (lowest increment) to 16.8% (highest increment).

The results demonstrate a superiority of CN-CRN mixture over CN and CRM (traditional creatine products) for increasing creatine bioavailability, serum creatine concentrations, and creatine distribution and absorption to the muscles in a cohort of young healthy men. CN-CRN blend appeared to be relatively safe, with no major disturbances of safety biomarkers for liver and kidney function, and/or subjectively reported adverse events.

Many innovative creatine supplements have been evaluated for effectiveness and safety during the past decade or so, with most products appeared inferior (or at least non-superior) in terms of utilization, bioavailability and performance to gold-standard CRM. For example, a buffered form of creatine was found less effective than CRM (Jagim et al.,

*J Int Soc Sports Nutr.* 2012; 9(1): 43), while several creatine analogs have shown significant side effects and limited applicability (Andres et al., *Mol Nutr Food Res.* 2017, 61(6)). Although CRM has been validated in many studies for its value and safety, it's use seems to be somewhat limited due to several technical or performance constraints, including its poor solubility in water, stability, bioavailability, and/or performance in specific conditions (Alraddadi et al, *Pharmaceutics.* 2018, 10(1): E31. and Writing Group for the NINDS Exploratory Trials in Parkinson Disease NET-PD Investigators. *JAMA.* 2015, 313: 584-93). Here, the addition of creatinine to supplemental creatine nitrate is shown to improve creatine utilization in the blood and skeletal muscle for both single-dose and 5-day intervention. Co-administration of creatine nitrate and creatinine shown favorable serum profiles, with the mixture improving body exposure to creatine for up to 52.1% comparing to CRM. This translates into greater muscle uptake of bioavailable creatine from the blood, with CN-CRN intervention (also CN) resulting in greater muscle creatine levels as compared to CRM.

Reaction 1

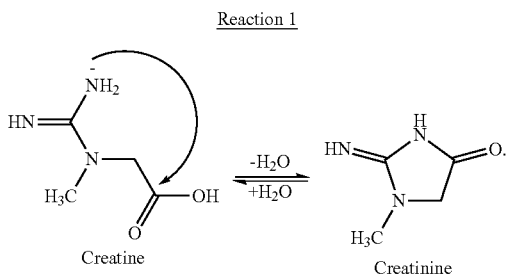

Creatine        Creatinine

The addition of creatinine to creatine nitrate possibly changes the chemical equilibrium in creatine-to-creatinine conversion in the blood, thus enhancing reverse reaction and an increase in serum creatine concentrations (Reaction 1), and perhaps higher saturation of cellular transporter for creatine (CRT1) that drives superior muscle consumption. Besides chemical equilibrium theory, CN-CRN might positively affect creatine uptake by virtue of other mechanisms, including enhanced muscle blood flow through provision of additional nitrate.

The transformation of creatine to creatinine is a reversible non-enzymatic reaction, where chemical equilibrium may be shifted by different factors such as changes in temperature, pH or the concentration of a reactant or a product. For example, the elevation of temperature, as well as the lowering of the pH, favors the formation of creatinine while creatine is favored at high pH and low temperature (Wyss and Kaddurah-Daouk, *Physiol Rev.* 2000, 80(3): 1107-1213). Specifically, changing the concentration of creatine or creatinine must follow Le Chatelier's principle, so any shift of equilibrium in the system canceled out by a responsive change to maintain equilibrium (Campbell, *J Chem Educ.* 1985, 62(3): 231). Here, a boosted concentration of creatinine induced by exogenous intake of creatine perhaps favored the equilibrium reaction toward creatine formation to decrease creatinine concentrations. This phenomenon has been confirmed for in vitro conditions, where creatinine may be hydrolyzed back to creatine in aqueous solutions, such as urine and blood, (Lempert, *Chem Rev.* 1959, 59(4): 667-736). On the other hand, an isotope-labeled study questioned the reversibility of the reaction changing creatine to creatinine in vivo (Bloch and Schoenheimer, *J Biol Chem.* 1939; 131(1): 111-119), where most of exogenous labeled creatinine was directly excreted into the urine while no significant exchange of the label with the body creatine was observed. This study provides the first indirect proof that creatinine might be hydrolyzed back to creatine in vivo when creatinine is co-administered with nitrate, as noted via favorable pharmacokinetics for serum creatine in a single-dose CN-CRN trial.

C. Side Effects and Non-Responders

No major adverse events after 5-day supplementation with CN-CRN mixture, besides a single-case of non-diarrheal bowel movements in an apparently sensitive participant, were reported. CN-CRN intervention did not alter liver enzymes levels, while eGFR seems to be moderately reduced (14.8%). No participant experienced serum creatinine levels>120 µmol/L at 5-day follow-up. The safety profile after short-term CN-CRN supplementation thus appears to be acceptable, and perhaps similar to CRM (Kreider et al., *J Int Soc Sports Nutr.* 2017, 14: 18).

In addition, CN-CRN appeared to favorably affect total muscle creatine concentrations in all recruited participants, while up to 30% of participants who received other two interventions (CN alone or CRM alone) remained non-responsive to creatine. The results in both CN and CRM trial are in agreement with previous studies that the prevalence of non-responders to creatine is about 25% (Kreider et al., 2017). The greater uptake of creatine by the skeletal muscle after CR-CRN intervention, even in participants who are creatine non-responders (have high initial level of muscle creatine who are otherwise immune to creatine supplementation), suggests that CR-CRN is most effective in providing creatine supplementation.

The invention claimed is:

1. A method of increasing creatine absorption in muscles in a human subject in need thereof, the method comprising co-administering to said human subject a supplemental amount of creatine, an effective amount of effective amount of creatinine, and a source of nitrate anion ($NO_3^-$), wherein the source of nitrate anion ($NO_3^-$) provides an effective amount of nitrate anion ($NO_3^-$).

2. The method of claim 1, wherein the human subject is a creatine non-responder.

3. The method of claim 1, wherein the co-administering comprises administering to the human subject a composition comprising:
the supplemental amount of creatine;
the effective amount of creatinine; and
the source of nitrate anion ($NO_3^-$).

4. The method of claim 1, wherein the supplemental amount of creatine is at least 500 mg, the effective amount of creatinine is at least 500 mg and the effective amount of the nitrate anion ($NO_3^-$) is at least 50 mg.

5. The method of claim 1, wherein the supplemental amount of creatine is at least 1000 mg, the effective amount of creatinine is at least 1000 mg, and the effective amount of nitrate anion ($NO_3^-$) is at least 100 mg.

6. The method of claim 1, wherein the supplemental amount of creatine is at least 2 grams, the effective amount of creatinine is at least 2 grams, and the effective amount of nitrate anion ($NO_3^-$) is at least 500 mg.

7. The method of claim 1, wherein the supplemental amount of creatine is at least 5 grams, the effective amount of creatinine is at least 3 grams, and the effective amount of nitrate anion ($NO_3^-$) is at least 1000 mg.

8. The method of claim 1, wherein the supplemental amount of creatine is at least between 500 mg and 20000 mg, the effective amount of creatinine is at between 500 mg and 30000 mg, and the effective amount of the nitrate anion ($NO_3^-$) is at between 50 mg and 3000 mg.

* * * * *